United States Patent
Lenormand et al.

(10) Patent No.: US 7,092,822 B2
(45) Date of Patent: Aug. 15, 2006

(54) METHOD OF EVALUATING THE CAPILLARY PRESSURE CURVE OF AN UNDERGROUND DEPOSIT ROCKS BASED ON ROCK CUTTINGS MEASUREMENTS

(75) Inventors: Roland Lenormand, Rueil Malmaison (FR); Patrick Egermann, Rueil Malmaison (FR); Daniel Longeron, Sartrouville (FR)

(73) Assignee: Institut Francais Du Petrole, Rueil Malmaison Cedex (FR)

( * ) Notice: Subject to any disclaimer, the term of this patent is extended or adjusted under 35 U.S.C. 154(b) by 78 days.

(21) Appl. No.: 10/514,414

(22) PCT Filed: May 14, 2003

(86) PCT No.: PCT/FR03/01456

§ 371 (c)(1), (2), (4) Date: Nov. 15, 2004

(87) PCT Pub. No.: WO03/098196

PCT Pub. Date: Nov. 27, 2003

(65) Prior Publication Data

US 2005/0216223 A1 Sep. 29, 2005

(30) Foreign Application Priority Data

May 15, 2002 (FR) .................................. 02 06003

(51) Int. Cl.
*G01N 15/08* (2006.01)
*G01N 33/24* (2006.01)

(52) U.S. Cl. ............................................. 702/9; 702/13

(58) Field of Classification Search .................... 702/9, 702/11, 12, 13
See application file for complete search history.

(56) References Cited

U.S. PATENT DOCUMENTS

| 4,211,106 | A | 7/1980 | Swanson |
| 4,648,261 | A | 3/1987 | Thompson et al. |
| 5,832,409 | A | 11/1998 | Ramakrishnan et al. |
| 2002/0029615 | A1 | 3/2002 | Lenormand et al. |

FOREIGN PATENT DOCUMENTS

| EP | 0 786 658 A1 | 7/1997 |
| GB | 2 354 590 A | 3/2001 |

*Primary Examiner*—Donald McElheny, Jr.
(74) *Attorney, Agent, or Firm*—Antonelli, Terry, Stout and Kraus, LLP.

(57) ABSTRACT

A method of evaluating the capillary pressure curve of rocks of an underground reservoir from measurements on rock debris or fragments such as cuttings from the reservoir, over the total saturation range of these rocks, within a short period and at a low cost, from these measurements is disclosed. The method comprises measuring the permeability k of the debris, measuring the capillary pressure curve Pc as a function of the saturation of these fragments initially saturated with a fluid (brine for example) by subjecting them to centrifugation, and parametrizing a capillary pressure curve Pc satisfying empirical relations depending on adjustable parameters, constrained to adjust to an asymptotic part of the capillary curve measured by centrifugation, and to the value of permeability k measured on the cuttings, so as to obtain the whole of the capillary pressure curve. Applications include hydrocarbon reservoir evaluation.

20 Claims, 4 Drawing Sheets

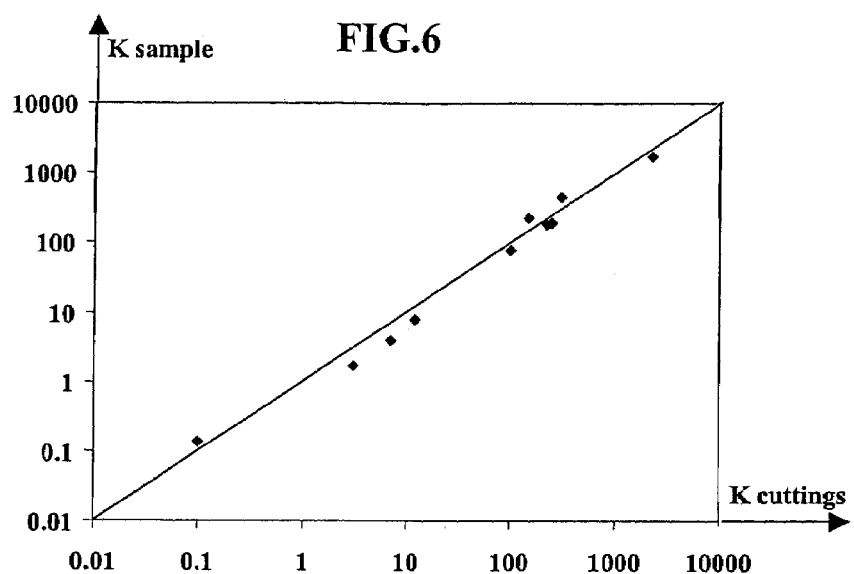
FIG.6
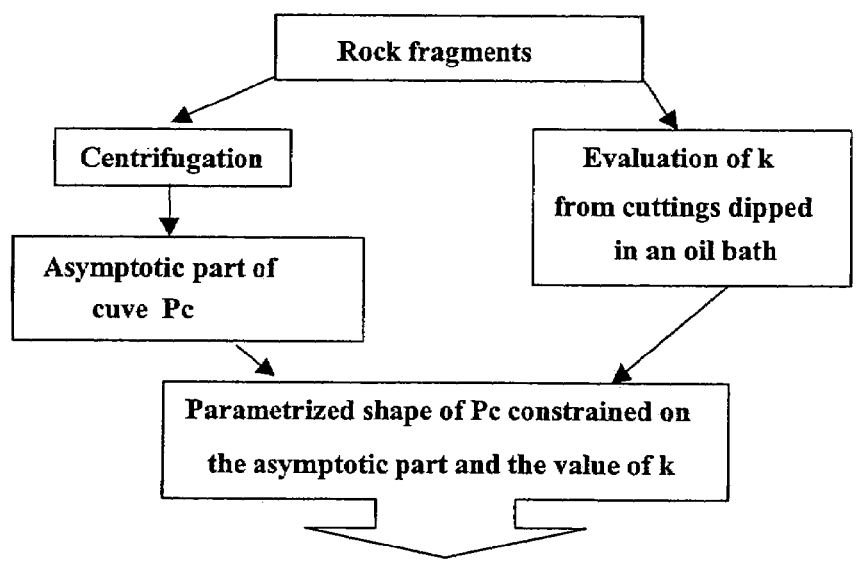
FIG.7
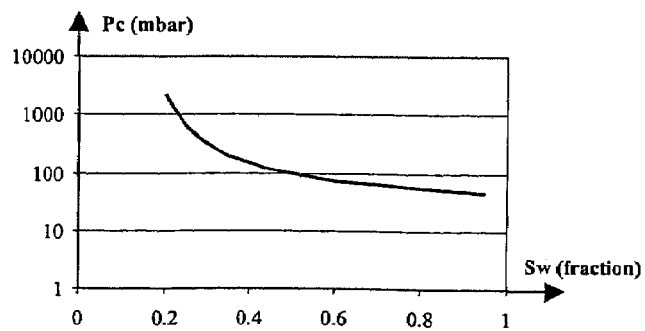

METHOD OF EVALUATING THE CAPILLARY PRESSURE CURVE OF AN UNDERGROUND DEPOSIT ROCKS BASED ON ROCK CUTTINGS MEASUREMENTS

BACKGROUND OF THE INVENTION

1. Field of the Invention

The present invention relates to a method of evaluating a capillary pressure curve of the rocks of an underground reservoir from measurements on rock debris taken therefrom.

2. Description of the Prior Art

Laboratory measurements on cores or cuttings

Measurement of petrophysical parameters such as the permeability, the porosity and the capillary properties on rock fragments obtained while drilling a well through an underground formation is an interesting opportunity for operator companies to rapidly obtain a first petrophysical characterization of producing zones traversed by the well.

French Patent 2,809,821, filed by the assignee, describes a system of evaluating physical parameters such as the absolute permeability of porous rocks of an underground reservoir zone, from cuttings returned to the surface in the drilling mud. In an enclosure where the cuttings are dipped in a viscous fluid, some of this fluid is injected at a pressure that increases with time until a predetermined pressure threshold is reached, so as to compress the gas trapped in the pores of the rock. This injection stage is followed by a relaxation stage where injection is stopped. The pressure evolution during the injection process is modelled from initial values selected for the physical parameters of the cuttings. A computer adjusts the values iteratively so as to obtain the best possible agreement between the modelled pressure curve and the pressure curve really measured.

French patent application 02/0023, filed by the assignee, describes another method of evaluating physical parameters such as the absolute permeability and the porosity of the rocks of an underground reservoir zone, also from cuttings. An enclosure containing the rock fragments and filled with a viscous fluid communicates with a vessel containing the same fluid at a predetermined pressure so as to compress the gas trapped in the pores of the rock. The time of application of this pressure, according to whether it is short or long, allows measuring either of the pressure variation in the enclosure or the variation of the volume actually absorbed by the rock fragments. The pressure or volume evolution in the enclosure is then modelled from initial values selected for the physical parameters of the fragments, and the values of the physical parameters of the rock fragments are iteratively adjusted so that the modelled evolution best adjusts to the measured evolution of the physical parameter in the enclosure.

In the field of petrophysical study, the capillary pressure is also a very important datum for operators because it conditions:

the initial distribution of the fluids in the reservoir from the aquifer zone (referred to as WOC, for water-oil contact, by those skilled in the art) to the upper part of the reservoir (transition zone). According to the capillary pressure curve associated with a reservoir rock and the nature of the fluids in place, this transition zone can extend over many meters, which has an important effect on the determination of the accumulations in place, the input pressure of a rock, which is particularly important for cap rocks. For example, for a gas storage tank, the input pressure of the cap rocks conditions directly the allowable overpressure in the storage levels without having leaks.

With the current techniques, the capillary pressure curve is obtained by means of laboratory measurements on reservoir cores. These methods are expensive because of the coring operations as well as the measurements on the cores, and the results are often available only several months after drilling.

Approaches to rapidly obtain the capillary pressure curve

However, there are alternative methods described in the literature for evaluating the capillary pressure curve rapidly, either during drilling or slightly later.

The most commonly used approach uses the mercury porosimetry technique for measuring the air/mercury capillary pressure curve Pc directly from cuttings. However, the obtained curve is significantly different from the reference curve obtained from cores with high wetting fluid saturations. Further, this approach is based on the use of mercury, which is extremely polluting and progressively forbidden by the law in many countries, which poses a major problem for applying this technique in the near future.

Another known method uses the Nuclear Magnetic Resonance (NMR) technique to rapidly estimate the capillary pressure curve from stratigraphic data measured in the well shortly after drilling. It is notably described in the following publications:

Bowers, M., A. et al.: "Prediction Of Permeability From Capillary Pressure Curves Derived With NMR", 17 Sep. 1998, Marshall, D., et al.: "Method For Correlating NMR Relaxometry And Mercury Injection Data", SCA No. Society of Core Analysts International Symposium 1995, Volokitin, Y., W. J. et al.: "A Practical Approach To Obtain $1^{st}$ Drainage Capillary Pressure Curves From NMR Core and Log Data", SCA No. Society of Core Analysts International Symposium 1999.

The NMR relaxation signal is first converted in terms of pore size distribution, then in terms of threshold size distribution, which allows calculation of a pseudo-capillary pressure curve. This approach has been tested on several samples of known curve Pc. The results show that a good agreement with the reference curves can only be obtained by means of a rigorous calibration stage to be carried out case by case according to the nature of the rocks studied. This calibration stage is necessary owing to the uncertainty on:

the NMR signal-pore size distribution conversion which depends on the value of the surface relaxivity which is variable according to the rocks, and the pore size distribution-threshold size distribution conversion which depends on the nature of the rock and on the diagenesis process.

This approach is therefore not recommended in a predictive exploration context. In any case, it would not be applicable to cuttings.

Image analysis has also been the subject of work intended to obtain a curve Pc. The porous medium is first prepared in a form of a thin section photographed by a scanning electron microscopy or SEM. The image obtained is then analyzed so as to determine parameters representative of the proportion and of the shape of the voids in relation to the rock. In particular, it is possible to determine a threshold size distribution to reconstruct a pseudo-capillary pressure curve Pc. The main limitation of this method is the two-dimensional (2D) nature of the thin section, whereas the capillary pressure is by definition a three-dimensional (3D) property. Besides, this technique requires quite heavy conditioning, which is not really compatible with a result obtained slightly later. Image analysis could be applicable to cuttings but it would require careful calibration to acquire a good predictability.

Finally, it can be noted that the centrifuging technique is sometimes applied in the field to cuttings in order to extract the largest possible amount of drilling fluid from the rock to minimize pollutant discharges to the environment and to limit the cost by recycling the drilling fluid recovered. The inventors do not know of centrifugation of cuttings having been considered in order to determine capillary properties.

SUMMARY OF THE INVENTION

The method according to the invention allows determination of the capillary pressure curve of rocks of an underground reservoir from measurements on rock debris or fragments (such as cuttings) taken therefrom, over the total saturation range of these rocks, within a short period and at a low cost, from these measurements. It comprises:

measuring the permeability k of the rock debris;

measuring the capillary pressure curve Pc as a function of the saturation of the rock debris initially saturated with a fluid by subjecting them to centrifugation; and parametrizing a capillary pressure curve Pc satisfying empirical relations depending on adjustable parameters, that is constrained to adjust to an asymptotic part of the capillary curve measured by centrifugation, and to the value of permeability k measured on the cuttings, so as to obtain a whole capillary pressure curve.

Parametrizing the curve is advantageously carried out by selecting by default a set of the parameters allowing calibration on the asymptotic part of the capillary pressure Pc with low saturations, and by modifying the parameters step by step so that the estimation of the permeability given by one of the empirical relations used is best adjusted with the measurements of permeability k carried out on rock debris with the asymptotic part.

Permeability k of the cuttings is measured for example from measurements of the pressure variations in a vessel filled with a fluid containing the cuttings after it has been coupled for a predetermined period of time with a tank containing the same fluid under pressure, and from the volume actually absorbed by the cuttings, and from modelling the evolution of the pressure or of the volume in the vessel, from initial values selected for the physical parameters of the cuttings, which are iteratively adjusted so that the modelled pressure evolution best adjusts with the measured evolution of the physical parameters of the cuttings.

The method is notably advantageous in that it provides the capillary pressure of the rocks on the basis of simple cuttings that are more readily available and less expensive to obtain. The results are also obtained much more rapidly than with cores.

BRIEF DESCRIPTION OF THE DRAWINGS

Other features and advantages of the method according to the invention will be clear from reading the description hereafter of an embodiment given by way of non limitative example, with reference to the accompanying drawings wherein:

FIG. 6 shows the comparison between the reference permeabilities and the permeabilities measured on cuttings within the scope of the method described in the aforementioned French patent application 02/0023; and FIG. 7 diagrammatically shows the flowchart for implementing the method.

DETAILED DESCRIPTION OF THE INVENTION

The method intended for fast evaluation of a capillary pressure curve Pc from rock fragments or cuttings according to the invention is illustrated by FIG. 7. The method is based on two experimental measuring stages, followed by a parametrizing stage by reference with known curves, to reconstruct curve Pc over the total saturation range. During one of the measuring stages, capillary pressure data Pc are acquired by centrifuging the initially water-saturated rock fragments. The other experimental stage allows calculation of the permeability value k of the rock from the method described in the aforementioned French patent application 02/0023. Reconstruction of curve Pc over the total saturation range is carried out by using a parametrized form. The parameters of the curve are determined in such a way that the curve matches the capillary pressure data Pc obtained experimentally and the estimated permeability value from the curve Pc obtained according to a known method such as Thomeer's or Swanson-Kamath's method, which are described below, with the value measured on the rock fragments. Several application cases are presented, with show the very good agreement obtained with reference curves without any particular previous calibration procedure.

I) Measurement of Pc by centrifugation from the cuttings

To implement the method, it is possible to use standard centrifugation means or more sophisticated means with automatic monitoring of the volumes of fluid produced, such as those described for example in patents EP-603,040 (U.S. Pat. No. 5,463,894), French patents 2,763,690, 2,772,477 (U.S. Pat. No. 6,185,985) or 2,798,734 filed by the assignee.

The cuttings which have come up to the surface during the drilling operation are first cleaned with solvents in a Soxhlet type device, then dried and saturated with 30 g/l brine. The cuttings are then drained in a damp cloth so as to remove the water trapped between the various cuttings d, then placed in a cell or cup fastened to the end of a rotating arm. The water expelled by centrifugation from the cuttings flows through a grate and it is collected at the base of the cup. The experimental data are acquired in the same way as in the context of centrifugation on a core. For a centrifugation stage (given rotating speed), the evolution of the water production is measured until no significant variation can be observed any longer, then the rotating speed is increased to start a new stage.

Figure 1:
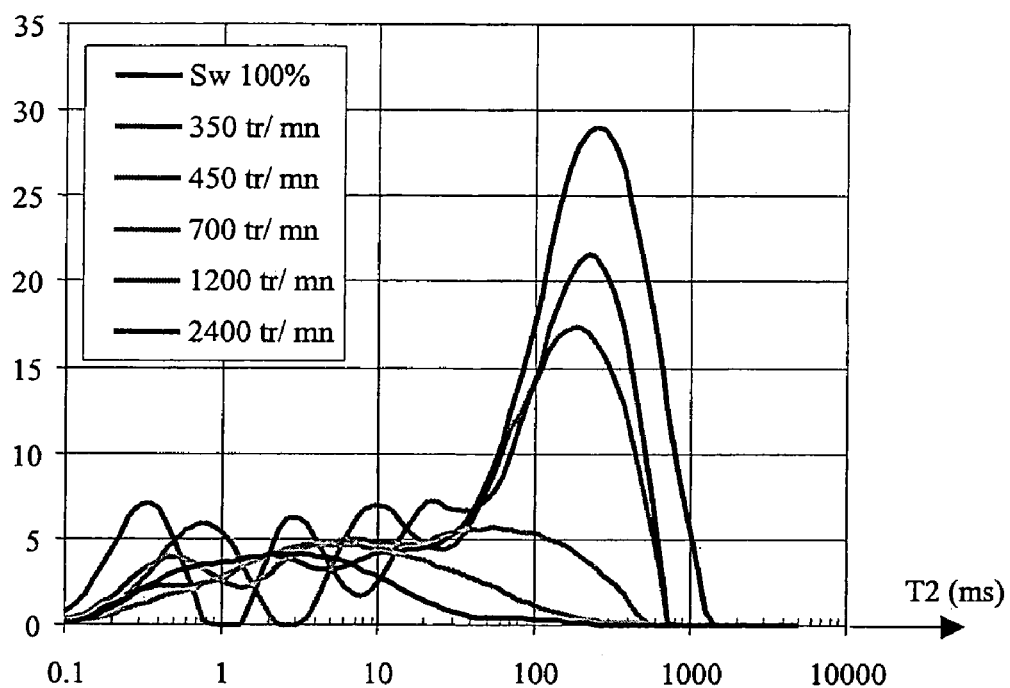
FIG. 1 shows the evolution of the NMR signal during various centrifugation stages carried out on cuttings.
Figure 2A:
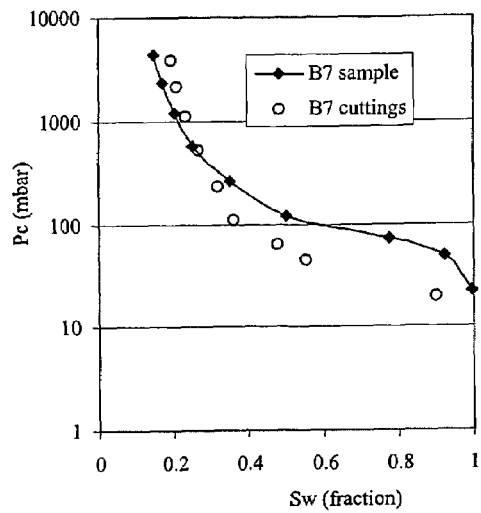
FIG. 2A shows the curves Pc obtained on a single rock (B7) from cuttings and from a core.
Figure 2B:
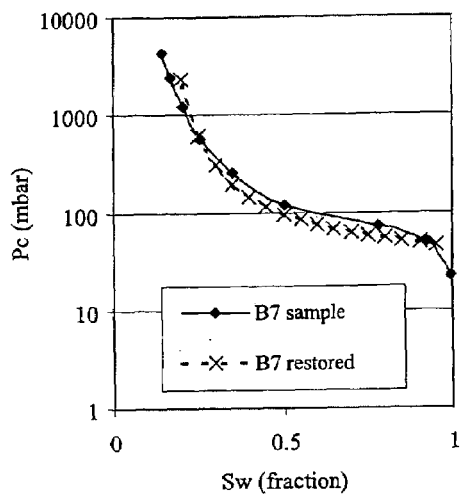
FIG. 2B shows the comparison between the reference curve Pc measured on a core and the reconstructed curve Pc over the total saturation range from the centrifugation measurements and the permeability measurement.
Figure 3A:
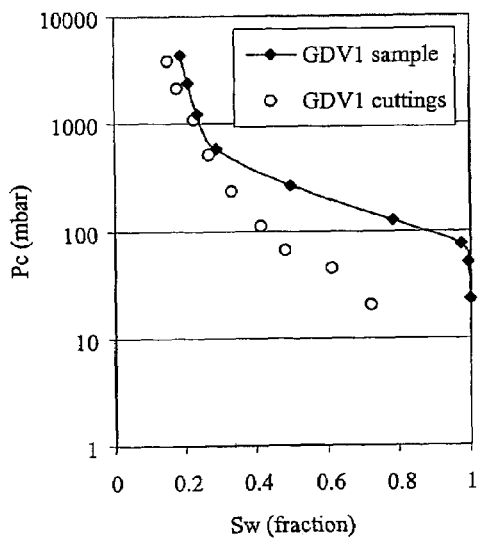
FIGS. 3A and 3B show results comparable to those shown in FIGS. 2A and 2B respectively for another rock GDV1.
Figure 3B:
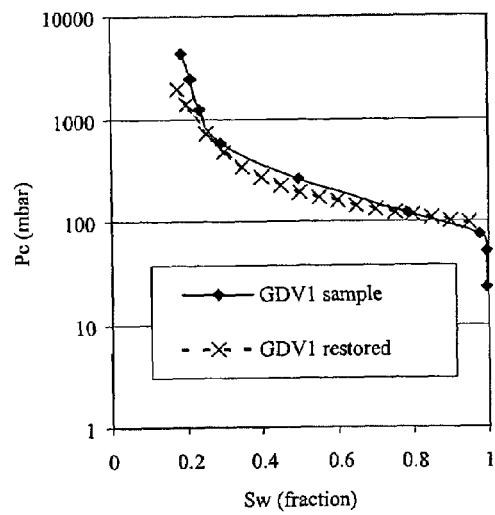
Figure 4A:
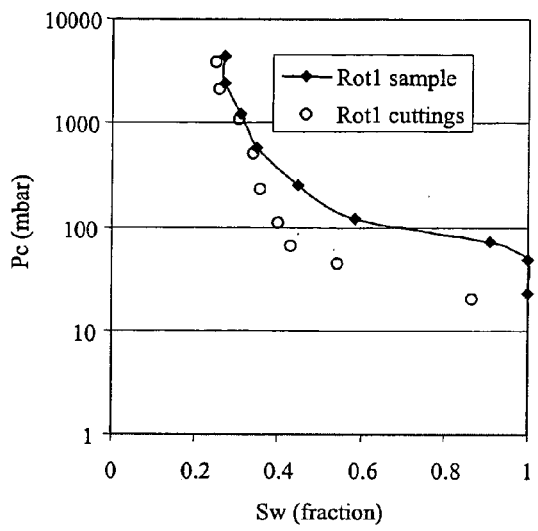
FIGS. 4A and 4B show results comparable to those shown in FIGS. 2A and 2B respectively for another rock Rot1.
Figure 4B:
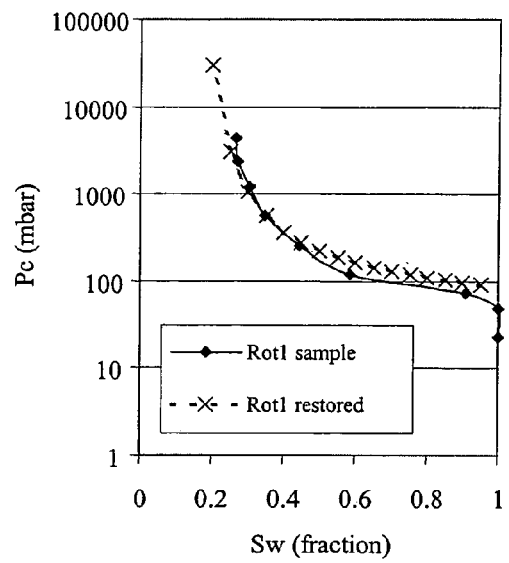
Figure 5A:
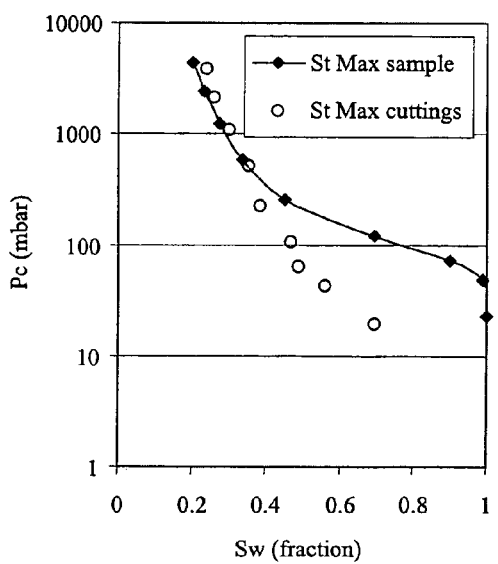
FIGS. 5A and 5B show results comparable to those shown in FIGS. 2A and 2B respectively for another rock St Max.
Figure 5B:
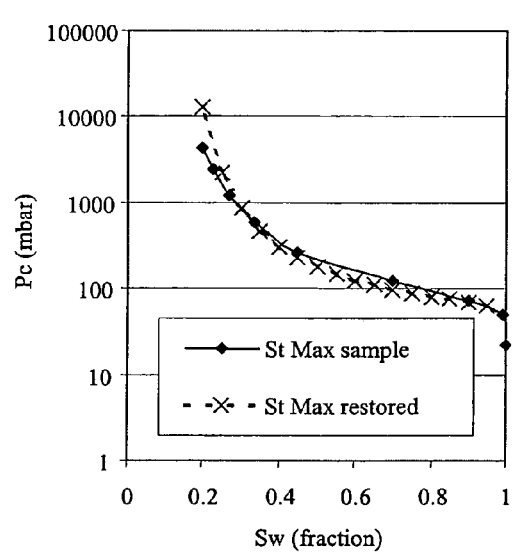

As can be seen in FIG. 1, a progressive decrease of the NMR signal and a shift to the short relaxation times T2 are observed, which express a desaturation of the porous medium with the increase of the rotating speed. This type of measurement shows that there definitely is a capillary contact between the cuttings, which allows to measure Pc by centrifugation from cuttings.

The volume of water produced during the experiment is converted to saturation data from the volume of water initially contained in the cuttings. The latter is determined by weighing (difference in the weight of the cuttings before and after saturation) or directly by NMR measurement.

FIGS. 2A to 5A show the result of experiments carried out from model cuttings, 1 to 2 mm in size, manufactured in the laboratory from rocks of known properties for which a curve Pc conventionally measured by centrifugation of a core is available. It can be seen that a good agreement is obtained with the reference curve at the level of the asymptotic part (low wetting fluid saturation). On the other hand, a big difference is observed for higher wetting fluid saturations. Results equivalent to those obtained within the context of porosimetry measurements using mercury on cuttings are thus obtained, without pollution risks.

The measured capillary pressure curve Pc is however representative only on the asymptotic part. A reconstruction procedure is therefore necessary to evaluate the behavior of the curve over the total saturation range.

II) Measurement of the permeability k of the cuttings

The method described in the aforementioned French patent application 02/02,242 is applied to measure the permeability of the cuttings. The cuttings are therefore dipped in a containment enclosure containing a viscous fluid. The enclosure is then coupled to a vessel containing the same fluid under pressure, so as to compress the gas trapped in the pores of the rock. According to a first embodiment, this communication period can be very short and followed, after a latency time, by the measurement of the pressure evolution in the enclosure. According to another embodiment, the communication period can be long enough to allow observing and measurement of the variation of the volume actually absorbed by the cuttings.

The evolution of the pressure or of the volume in the enclosure is then modelled from initial values selected for the physical parameters of the cuttings, and the values of the physical parameters of the cuttings are iteratively adjusted so that the modelled evolution best adjusts with the measured evolution of the physical parameter in the enclosure.

This procedure gives excellent results. The permeability values k of the cuttings are totally in accordance with the reference measurements obtained from cores.

III) Reconstruction of the total capillary pressure curve

In this third stage, the previous measurements are synthesized that have allowed construction of the asymptotic part of the capillary pressure curve Pc and the measurements of permeability k using empirical relations to model as well the physical parameters of rocks. The following publications:

Thomeer, J. H. M.: "Introduction Of A Pore Geometrical Factor Defined By The Capillary Pressure Curve", Trans AIME, vol. March, pp. 73–77, 1960, and Thomeer, J. H. M.: "Air Permeability As A Function Of Three Pore Network Parameters", Trans AIME, vol. April, pp. 809–814, 1983 describe methods for evaluating the permeability from a capillary pressure curve. A capillary pressure curve Pc is modelled in the following form:

$$P_c = P_d \times \exp\left(-\frac{G}{\operatorname{Ln}\left(\frac{V_b(P_c)}{V_b(P_\infty)}\right)}\right)$$

where:

G is a shape parameter for accounting for the curvature of the capillary pressure curve (related to the shape of the pore size distribution);

$P_d$ is the displacement pressure extrapolated to $S_{Hg}$ equal to zero; and $V_{b\infty}$ is the percentage of volume occupied by the mercury at the end of the experiment at an infinite capillary pressure (equal to $\phi \times S_{Hg}$). The three parameters of the model being related to the permeability by the following expression:

$$k = 3.8068 \times G^{-1.334} \times \left[\frac{V_{b\infty}}{P_d}\right]^2.$$

In the following publication:

Swanson, B. F.: "A Simple Correlation Between Permeability And Mercury Capillary Pressures", JPT, vol. December, pp. 2498–2504, 1981, the author proposes correlating the value of the permeability with the maximum value of ratio ($V_b/P_c$) on the mercury porosimetry curve. This particular point generally corresponds to the regime change that occurs at the end of the percolation regime, just before the significant capillary pressure increase. As regards the capacity of fluid flow in the porous medium, this point is particularly important because it represents the pore size for which the entire pore network is connected and which therefore controls the flow. The most general correlation provided by the author is given by the expression (Swanson 1981):

$$k = 355 \times \left(\frac{V_b}{P_c}\right)_A^{2.005}$$

The following publication:

Kamath, J.: "Evaluation Of Accuracy Of Estimating Air Permeability From Mercury Injection Data", SPE Formation evaluation, vol. 7,4, pp. 304–310, 1992 also relates to the comparative evaluation of the approaches using empirical correlation or physical models to determine the permeability value from a mercury porosimetry curve. The best agreement is obtained with a new correlation based on the aforementioned characteristic length by Swanson 1981, mentioned above:

$$k = 413 \times L_{\max}^{1.85} \text{ if } k < 1 \text{ mD}$$
$$k = 347 \times L_{\max}^{1.60} \text{ if } k > 1 \text{ mD},$$

$L_{max}$ being defined as follows:

$$L_{\max} = \left(\frac{\phi \times S_{nw}}{P_c}\right)_{\max} = \frac{\phi \times \lambda \times (100 - S_r)}{P_e \times (1+\lambda)^{\frac{1}{\lambda}+1}} \text{ and } \left(\frac{P_e}{P_c}\right)^\lambda = \frac{S_w - S_r}{100 - S_r}$$

where:

λ: exponent expressing the curvature of the capillary pressure curve (related to the shape of the pore size distribution), $P_c$: the displacement pressure extrapolated to $S_{Hg}$ equal to zero, and $S_r$: residual saturation occupied by the wetting fluid (%).

To parametrize the empirical capillary pressure curve Pc obtained from Thomeer's, Swanson's or Kamath's approaches, it is constrained to adjust to the asymptotic part obtained by centrifugation during the first stage of the method. The entire curve is constrained using also the value of permeability k measured on cuttings during the second stage of the method, which is compared with the result of the empirical relations. The parameters of the capillary pressure Pc are then modified until both the measured asymptotic behavior and the permeability estimation are met, which allows constraining the capillary pressure curve over the total saturation range Sw.

The inversion process starts with a set of default parameters which allow calibration of the asymptotic behavior of the capillary pressure Pc with low water saturations. These parameters are then modified step by step (mainly the input pressure Pe or Pd and the shape factor λ or G) so that the estimation of the permeability given by one of the previous relations is in good agreement with the permeability measurement obtained on cuttings while keeping a good agreement with the measurements of Pc at low water saturations.

1.1 Results obtained

FIGS. 2B, 3B, 4B and 5B show the comparison between the curve Pc reconstructed according to the previous procedure and the reference curve Pc obtained on a core. It can be seen that, whatever the example considered, the reconstruction method allows obtaining a pertinent evolution of Pc over the total saturation range and in particular at high water saturations, whatever the permeability of the rock.

| Name | K (mD) | G | Vb (fraction) | Pe (bar) |
|---|---|---|---|---|
| Rot1 | 150 | 0.28 | 0.89 | 0.38 |
| GDV1 | 195 | 0.28 | 1.00 | 0.41 |
| B7 | 780 | 0.25 | 0.92 | 0.2 |
| StMax | 2000 | 0.34 | 0.92 | 0.26 |

The invention claimed is:

1. A method of determining a capillary pressure curve of rocks of an underground reservoir from measurements on cuttings taken therefrom, by measuring a permeability of cuttings, comprising:
   measuring the capillary pressure curve as a function of saturation by subjecting the cuttings, initially saturated with a fluid, to centrifugation; and
   parametrizing the capillary pressure curve satisfying empirical relations depending on adjustable parameters, constrained to an asymptotic part of the capillary curve measured by centrifugation, and to a value of the permeability measured on the cuttings, so as to obtain a capillary pressure curve.

2. A method as claimed in claim 1, comprising:
   selecting by default a set of the parameters allowing calibration on an asymptotic part of the capillary pressure curve and modifying parameters so that an estimation of the permeability given by one of the empirical relations is adjusted with permeability measurements carried out on the cuttings with the asymptotic part.

3. A method as claimed in claim 1, wherein the permeability of the cuttings is measured from measurements of pressure variations in a vessel filled with a fluid containing the cuttings after the vessel has been coupled for a predetermined period of time to a source of fluid containing the cuttings under pressure, a volume absorbed by the cuttings, and modelling an evolution of the pressure or of the volume of the vessel, from initial values selected for a physical parameters of the cuttings, which are iteratively adjusted so that a modelled pressure evolution adjusts with a measured evolution of the physical parameters of the cuttings.

4. A method in accordance with claim 1 wherein:
   the asymptotic part has low saturation.

5. A method in accordance with claim 2 wherein:
   the asymptotic part has low saturation.

6. A method in accordance with claim 3 wherein:
   the asymptotic part has low saturation.

7. A method in accordance with claim 1 wherein the modelled pressure evolution best adjusts with a measured evolution of physical parameters of the cuttings.

8. A method in accordance with claim 2 wherein the modelled pressure evolution best adjusts with a measured evolution of physical parameters of the cuttings.

9. A method in accordance with claim 3 wherein the modelled pressure evolution best adjusts with a measured evolution of physical parameters of the cuttings.

10. A method in accordance with claim 4 wherein the modelled pressure evolution best adjusts with a measured evolution of physical parameters of the cuttings.

11. A method in accordance with claim 5 wherein the modelled pressure evolution best adjusts with a measured evolution of physical parameters of the cuttings.

12. A method in accordance with claim 6 wherein the modelled pressure evolution best adjusts with a measured evolution of the physical parameters of the cuttings.

13. A method in accordance with claim 1 wherein a whole capillary pressure curve is obtained.

14. A method in accordance with claim 2 wherein a whole capillary pressure curve is obtained.

15. A method in accordance with claim 3 wherein the source of fluid is a tank.

16. A method in accordance with claim 4 wherein the source of fluid is a tank.

17. A method in accordance with claim 5 wherein the source of fluid is a tank.

18. A method in accordance with claim 6 wherein the source of fluid is a tank.

19. A method in accordance with claim 7 wherein the source of fluid is a tank.

20. A method in accordance with claim 8 wherein the source of fluid is a tank.

* * * * *